United States Patent [19]

Nadkarni et al.

[11] Patent Number: 5,571,701
[45] Date of Patent: Nov. 5, 1996

[54] ANTIBIOTIC, BALHIMYCIN, A PROCESS FOR ITS PRODUCTION AND ITS USE AS PHARMACEUTICAL

[75] Inventors: Suresh R. Nadkarni; Sugata Chatterjee; Mahesh V. Patel, all of Bombay; Kalvanapuram R. Desikan, L.B. S. Mang. Mulund; Erra K. S. Vijayakumar; Bimal N. Ganguli, both of Bombay, all of Ind.; Jürgen Blumbach, Niedernhausen, Germany; Hans-Wolfram Fehlhaber, Idstein/Taunus, Germany; Herbert Kogler, Kelkheim/Taunus, Germany

[73] Assignee: Hoechst Aktiengesellschaft, Frankfurt am Main, Germany

[21] Appl. No.: 449,543

[22] Filed: May 24, 1995

Related U.S. Application Data

[60] Division of Ser. No. 996,936, Dec. 30, 1992, Pat. No. 5,451,570, which is a continuation-in-part of Ser. No. 735,891, Jul. 25, 1991, abandoned.

[30] Foreign Application Priority Data

Jul. 27, 1990 [EP] European Pat. Off. ............. 90114471
Oct. 17, 1990 [EP] European Pat. Off. ............. 90119883

[51] Int. Cl.$^6$ .............................. C12P 21/04; C12N 1/20; C07K 9/00; A61K 38/14
[52] U.S. Cl. .......................... 435/71.3; 435/252.1; 514/8; 530/317; 530/322
[58] Field of Search ............................... 435/71.3, 252.1; 530/317, 322; 514/8

[56] References Cited

U.S. PATENT DOCUMENTS

| | | |
|---|---|---|
| 3,067,099 | 12/1962 | McCormick et al. . |
| 4,698,327 | 10/1987 | Nagarajan et al. . |
| 4,742,045 | 5/1988 | Verma et al. . |
| 5,187,082 | 2/1993 | Hamill et al. . |

FOREIGN PATENT DOCUMENTS

| | | |
|---|---|---|
| 0301785A2 | 2/1989 | European Pat. Off. . |
| WO91/16346 | 10/1991 | WIPO . |

OTHER PUBLICATIONS

D. H. Williams, et al., "Part B–The Vancomycin and Ristocetin Group of Antibiotics," Topics in Antibiotic Chemistry, vol. 5:123–158 (1980).
R. D. Sitrin, et al., "Aridicins, Novel Glycopeptide Antibiotics," Journal of Antibiotics, vol. 38(5):561–571 (1985).
T. Takatsu, et al., "Chloropolysporins A, B and C, Novel Glyocopeptide Antibiotics From Faenia Interjecta Sp. Nov.," Journal of Antibiotics, vol. 40(7):924–932 (1987).
R. Nagarajan, et al., "Conversion of Antibiotic A82846B to Orienticin A and Structural Relationships of Related Antibiotics," Journal of Organic Chemistry, vol. 54:983–986 (1989).

Merck Index, p. 1561:9836 (11th Ed. 1989).

Primary Examiner—Herbert J. Lilling
Attorney, Agent, or Firm—Finnegan, Henderson, Farabow, Garrett & Dunner, L.L.P.

[57] ABSTRACT

Balhimycin, a compound of the molecular formula $C_{66}H_{73}Cl_2N_9O_{24}$, is a novel Glycopeptide antibiotic and has the following structure:

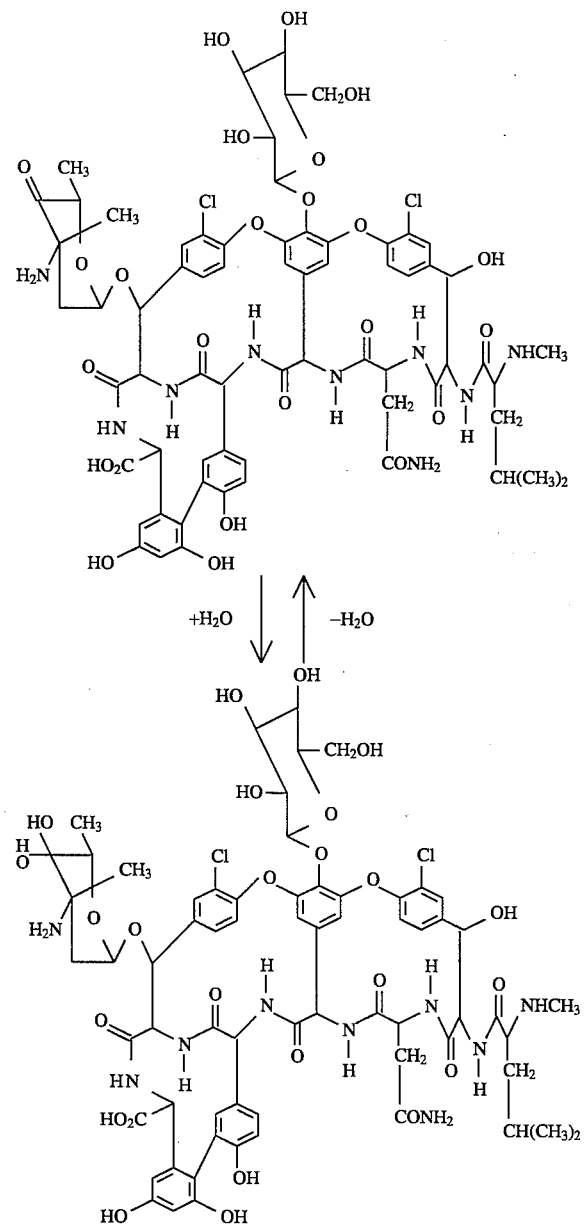

10 Claims, 5 Drawing Sheets

RETENTION TIME IN MINUTES

13C-NMR-SPECTRUM Balhimycin
IN [D$_6$]-DMSO. T = 320 K. c = 28 mg/ml

| SIGNAL | MULT | CHEM. | SIGNAL | MULT | CHEM. |
|---|---|---|---|---|---|
| 1 | s | 211.47 | 34 | d | 116.13 |
| 2 | s | 174.34 | 35 | d | 107.91 |
| 3 | s | 171.97 | 36 | d | 105.94 |
| 4 | s | 170.95 | 37 | d | 104.61 |
| 5 | s | 170.24 | 38 | d | 102.54 |
| 6 | s | 169.28 | 39 | s | 102.45 |
| 7 | s | 169.15 | 40 | d | 102.18 |
| 8 | s | 167.08 | 41 | d | 93.62 |
| 9 | s | 166.49 | 42 | d | 77.38 |
| 10 | s | 156.90 | 43 | d | 76.54 |
| 11 | s | 156.21 | 44 | d | 74.37 |
| 12 | s | 154.93 | 45 | d | 74.17 |
| 13 | s | 151.39 | 46 | d | 74.12 |
| 14 | s | 150.95 | 47 | d | 71.09 |
| 15 | s | 150.19 | 48 | d | 69.99 |
| 16 | s | 149.24 | 49 | d | 62.18 |
| 17 | s | 139.62 | 50 | t | 61.08 |
| 18 | s | 137.50 | 51 | d | 60.58 |
| 19 | s | 136.29 | 52 | d | 58.19 |
| 20 | d | 135.50 | 53 | d | 56.67 |
| 21 | s | 133.83 | 54 | s | 55.72 |
| 22 | s | 132.31 | 55 | d | 54.66 |
| 23 | d | 128.73 | 56 | d | 53.53 |
| 24 | d | 128.30 | 57 | d | 50.88 |
| 25 | d | 127.47 | 58 | t | 42.92 |
| 26 | s | 126.75 | 59 | t | 40.93 |
| 27 | d | 126.63 | 60 | t | 36.99 |
| 28 | s | 125.75 | 61 | q | 33.66 |
| 29 | d | 125.38 | 62 | d | 28.55 |
| 30 | d | 124.21 | 63 | q | 24.05 |
| 31 | d | 123.41 | 64 | q | 22.85 |
| 32 | s | 121.60 | 65 | q | 22.14 |
| 33 | s | 117.76 | 66 | q | 15.25 |

FIG. 5

ANTIBIOTIC, BALHIMYCIN, A PROCESS FOR ITS PRODUCTION AND ITS USE AS PHARMACEUTICAL

This is a division of application Ser. No. 07/996,936, filed Dec. 30, 1992, now U.S. Pat. No. 5,451,570 which is a continuation-in-part of application Ser. No. 07/735,891, filed Jul. 25, 1991, now abandoned.

This invention relates to a new glycopeptide antibiotic named Balhimycin from an Actinomycete culture number Hoechst India Limited Y-86,21022. Balhimycin may be described as an antibacterial antibiotic belonging to the glycopeptide class. Glycopeptide antibiotics are narrow-spectrum antibiotics acting mainly against Gram positive bacteria. Their activity against methicillin resistant $S.$ $aureus$ (MRSA) strains make them a valuable drug in treating infections caused by MRSA. They are also useful as growth promoters in the veterinary field. Glycopeptide antibiotics are described in Topics in Antibiotic Chemistry, Vol. 5, page 119 (1980), Journal of Antibiotics, Vol. 38, page 561 (1985), Journal of Antibiotics Vol. 40, page 924 (1987), Journal of Organic Chemistry, Vol. 54, page 983 (1989).

However, Balhimycin described herein differs from all the known glycopeptide antibiotics in its molecular formula and therefore forms the subject of this invention. Furthermore a Chemical Abstracts on-line search performed with the search keys of molecular weight and molecular formula confirms the novelty of the compound.

The microorganism, culture No. Hoechst India Limited, Y-86,21022, henceforward referred to as Y-86,21022, used for the production of Balhimycin was isolated from a soil sample collected at Thamu forest, Himalaya, India. The microorganism, Y-86,21022, belongs to the order Actinomycetales. The microorganism Y-86,21022 has been deposited with Deutsche Sammlung von Mikroorganismen under the conditions of the Treaty of Budapest on Apr. 6, 1990 and it has received No. DSM 5908.

A further aspect of the present invention is to provide a process for the production of the new antibiotic Balhimycin from culture No. Hoechst India Limited Y-86,21022, its mutants and variants. The said process comprises cultivation of culture Y-86,21022, its mutants and variants under aerobic conditions in a nutrient medium containing sources of carbon and nitrogen, nutrient inorganic salts and trace elements and isolation and purification of the said antibiotic from the culture broth. The carbon sources may be starch, glucose, sucrose, dextrin, fructose, molasses, glycerol, lactose or galactose. The preferred carbon source is glycerol. The sources of nitrogen may be soyabean meal, peanut meal, yeast extract, beef extract, peptone, malt extract, corn steep liquor, gelatin or casamino acids. The preferred nitrogen source is soyabean meal. Nutrient inorganic salts may be sodium hydrogen phosphate, potassium hydrogen phosphate, sodium chloride, calcium chloride, calcium carbonate, potassium nitrate, ammonium sulphate or magnesium sulphate. Trace elements could be salts of iron, manganese, copper, zinc or cobalt or other heavy metals.

Cultivation of culture No. Y-86,21022 is preferably carried out at temperatures between 28° and 32° C. and ph between 6.0 and 8.0. In particular culture No. Y-86,21022 is cultivated at 29° C. (±1° C.) and ph about 7.0.

The fermentation is carried out preferably for 60 to 72 hours when optimal yield of the antibiotic of the present invention is obtained. Fermentation is particularly carried out for 68–72 hours under submerged conditions in shake flasks as well as in laboratory fermenters. If desired, an anti-foam agent such as Desmophen® (Polyols, Bayer-AG Leverkusen, West Germany) can be used in the fermenters. The progress of fermentation and formation of the compound according to present invention can be detected by High Pressure Liquid Chromatography (HPLC) and by measuring the bioactivity of the culture broth against Staphylococci species by the known microbial agar plate diffusion assay method. The preferred culture is $Staphylococcus$ $aureus$ 3066 known to be resistant to Methicillin, a beta-lactam antibiotic reported in the literature.

Balhimycin can for example be isolated from the culture broth by direct adsorption on suitable adsorbants like activated carbon, Diaion HP-20® (high porosity resin based on a polystyrene-divinylbenzene copolymer—Mitshubishi Chemical Industries, Japan) or Amberlite®XAD (porous resin based on polystyrene-acrylic acid ester—Rohm & Haas Co., U.S.A.). The preferred adsorbent is Diaion HP-20. Balhimycin can be eluted out of these adsorbents using mobile phases such as water, methanol, acetone, acetonitrile or suitable combinations thereof. The preferred eluants are aqueous methanol or acetone.

The aforementioned active eluates containing Balhimycin can be concentrated and can be further purified in a number of ways. For example, readsorption and elution processes with activated charcoal, Amberlite XAD-4 and 7, Diaion HP-20; gel filtration with Sephadex LH-20®, or G series gels (Pharmacia Fine Chemicals AB, Sweden) using water, methanol, acetone or appropriate combinations thereof as eluants; ion-exchange chromatography with IRC-50 ($H^+$) at Ph range of 6.5–8.5 using 0.1N Hcl as the eluant; or medium pressure liquid chromatography (MPLC) on suitable adsorbents like silica, modified silica such as reverse phase silica, for example octadecyldimethylsilylated silica (RP-18), neutral alumina. Furthermore countercurrent chromatography with a given multicomponent solvent system may also be used for the said purpose. The preferred method of purification includes repeated MPLC on RP-18 using aqueous methanol or acetonitrile containing suitable additive such as salt or acid, as the eluant.

Balhimycin can be converted into its pharmacologically acceptable salts, for example, with inorganic and organic acids such as HCl, $H_2SO_4$, citric acid, lactic acid, succinic acid, acetic acid, trifluoro acetic acid in a known manner.

BRIEF DESCRIPTION OF THE DRAWING

FIG. 5 shows the $^{13}$C-NMR spectrum of Balhimnycin.

Figure 1:
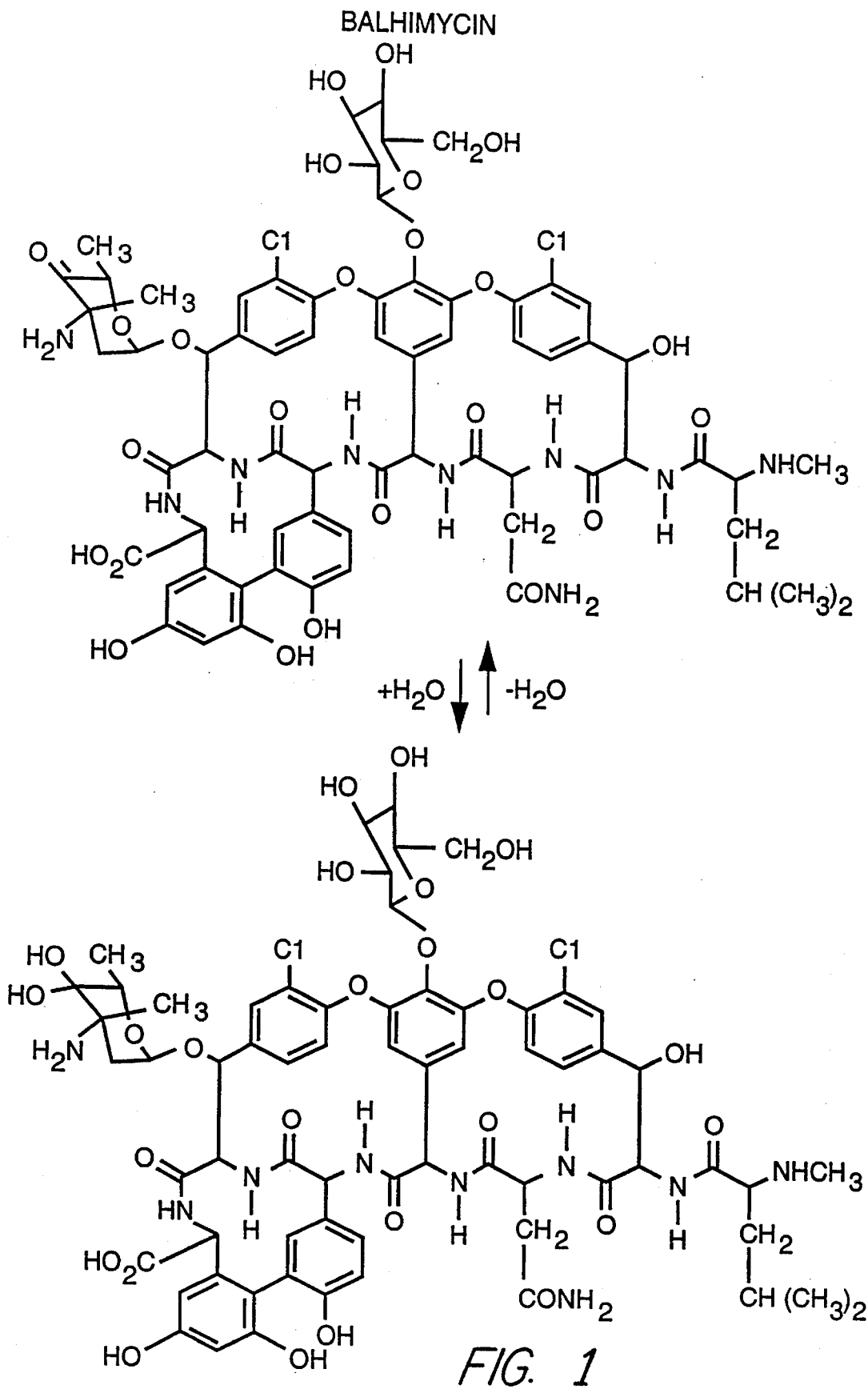
FIG. 1 shows the structure of Balhimycin.

The physico-chemical and spectral properties of Balhimycin are shown in Table 1 below. The structure of Balhimycin is shown in FIG. 1.

TABLE 1

| Physic chemical and spectral properties of Balhimycin (as its trifluoroacetate salt) | |
|---|---|
| Nature | White powder |
| Chemical type | Basic glycopeptide of the vancomycin class |
| Solubility | Water, dimethylsulfoxide |
| M. pt. | >300° C. (decomposition) |
| $[\alpha]_D^{22}$ | −23.2 ± 2° (C = 5, $H_2O$) |
| High Pressure Liquid | 4.2 minutes, 4 × (250 + 30) |

TABLE 1-continued

Physic chemical and spectral properties of Balhimycin (as its trifluoroacetate salt)

Figure 2:
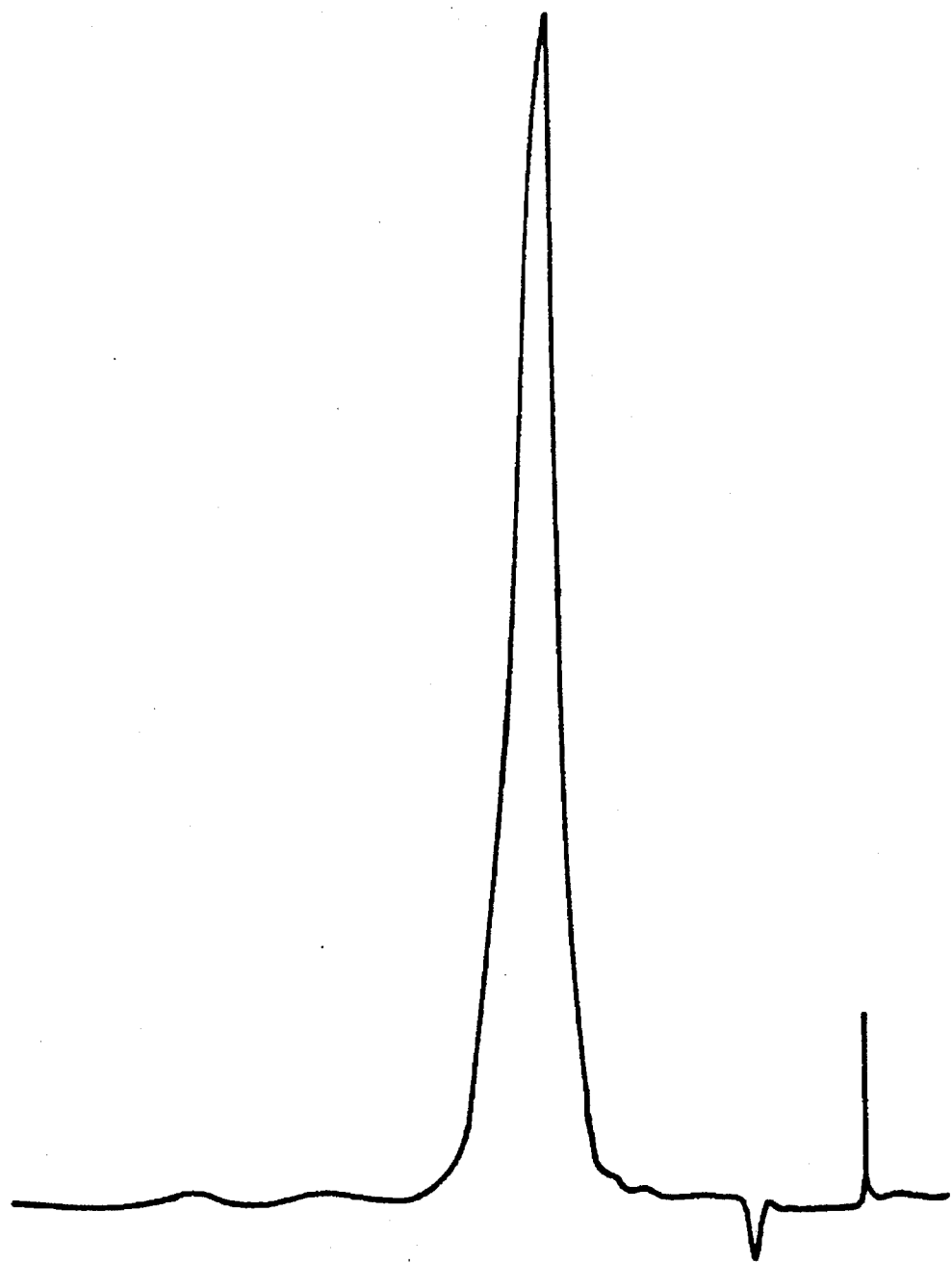
FIG. 2 shows the HPLC retention time of Balhimycin.
Figure 3:
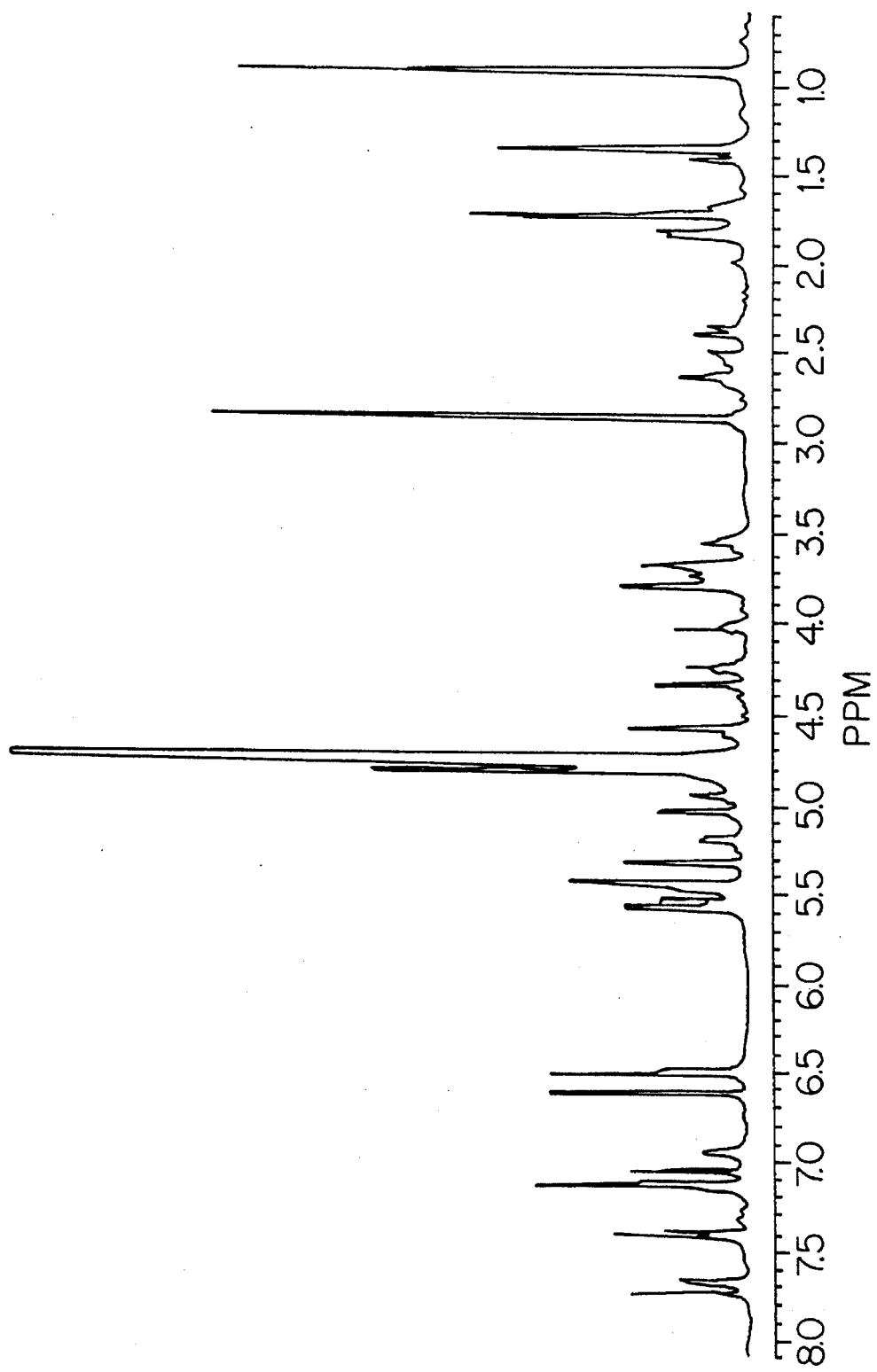
FIG. 3 shows the $^1$H NMR of Balhimycin at 400 MHz $D_2O$, 300K.
Figure 4:
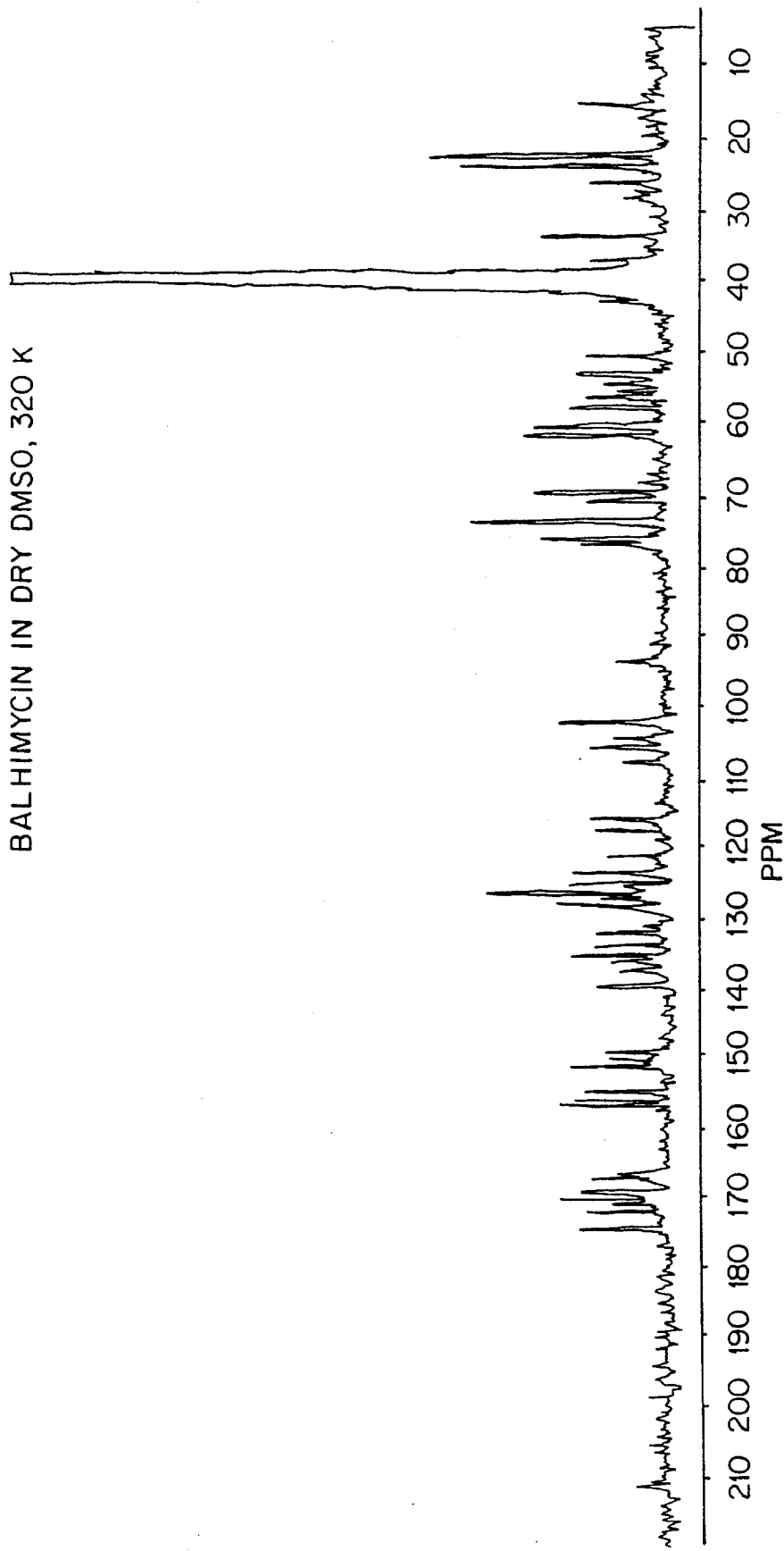
FIG. 4 shows the $^{13}$C-NMR of Balhimycin in dry DMSO, 320K.

| | |
|---|---|
| Chromatography (HPLC) Retention Time | mm 10μ "ODS-Hypersil" column, eluant 18% acetonitrile in water containing 0.1% TFA, flow rate 2 ml/minute, detection 220 nm, chart speed 10 mm/minute, FIG. 2 of the accompanying drawings |
| Molecular Formula | $C_{66}H_{73}Cl_2N_9O_{24}$ determined by high resolution FAB mass spectrometry (M + H$^+$ measured m/z 1446.4204, calculated m/z 1446.4205 for $^{12}C_{66}{}^{1}H_{74}{}^{35}Cl_2{}^{14}N_9{}^{16}O_{24}$) |
| UV$_{max}$ (H$_2$O) | 208, 285 nm |
| $^1$H NMR (400 MHz D$_2$O, 300K) | FIG. 3 of the accompanying drawings |
| $^{13}$C-NMR (Dry DMSO, 320K) | FIG. 4 of the accompanying drawings |
| $^{13}$C-NMR-Spectrum | FIG. 5 of the accompanying drawings |

Balhimycin and its physiologically tolerated salts can be administered, for example, orally, intramuscularly or intravenously. Pharmaceuticals which contain Balhimycin as active substance are subject of the present invention also. They can be prepared by mixing the said compound with one or more pharmacologically tolerated auxiliaries and/or excipients such as, for example, fillers, emulsifiers, lubricants, masking flavours, colorants or buffer substances, and converted into a suitable pharmaceutical form such as, for example, tablets, coated tablets, capsules, or a suspension or solution suitable for parenteral administration.

Examples of auxiliaries and/or excipients which may be mentioned are tragacanth, lactose, talc, agar-agar, polyglycols, ethanol and water. Suitable and preferred for parenteral administration are suspension or solutions in water. It is also possible to administer the active substances as such, without vehicles or diluents, in a suitable form, for example in capsules.

Suitable doses of the compound of this invention or its physiologically tolerated acid addition salts are about 0.1 to 20 g/day, preferably 0.5 to 4 g/day, for an adult of body weight about 60 kg.

It is possible to administer single doses or, in general, multiple doses, it being possible for the single dose to contain the active substance in an amount of about 50 to 4,000 mg, preferably of about 500 to 2,000 mg.

The instant invention is further characterized by the following examples and by the content of the patent claims.

EXAMPLE 1

Isolation of the culture Y-86,21022 from soil (a) Composition of nutrient isolation medium

| | |
|---|---|
| Corn starch | 10.0 g |
| Casein | 1.0 g |
| Peptone | 1.0 g |
| Yeast Extract | 1.0 g |
| K$_2$HPO$_4$ | 0.5 g |
| Agar powder | 13.0 g |
| Demineralized water | 1.0 liter |
| Ph | 7.5 |

(b) Soil plating and isolation 10 g of soil collected from Thamu Forest, Himalaya, India were added to 90 ml of sterilized demineralized water in a 250 ml Erlenmeyer flask which was shaken for 2 hours on a rotary shaker (220 rpm). The above soil suspension was then serially diluted in steps of 10 upto ($10^{-5}$). From the last dilution, 1 ml of suspension was placed at the centre of a sterile glass petri plate (15 cms diameter) to which was then poured approximately 50 ml of the above isolation medium supplemented with 25 mcg/ml of amphotericin B as anti fungal agent and cooled to 45° C. and the plate swirled thoroughly. The mixture of soil suspension and medium was allowed to settle and incubated at 28° C. (±1° C.) for 7 days. The petri plate was periodically observed and the culture No. Y-86,21022 was isolated from amongst the growing microorganisms.

EXAMPLE 2

Maintenance of the culture Y-86,21022

Composition of maintenance medium

Culture No. Y-86,21022 was maintained on the following medium

| | |
|---|---|
| Malt Extract | 10.0 g |
| Yeast Extract | 4.0 g |
| Glucose | 4.0 g |
| Agar Powder | 13.0 g |
| Demineralized water | 1.0 liter |
| pH | 7.0 |

After dissolving the ingredients thoroughly by heating, it was distributed in test tubes and then sterilized at 121° C. for 20 minutes. The test tubes were cooled and allowed to solidify in a slanting position. The agar slants were streaked with the growth of the culture No. Y-86,21022 by a wire loop and incubated at 28° C. (±1° C.) until a good growth was observed. The well grown cultures were stored in the refrigerator at +8° C.

EXAMPLE 3

Fermentation of culture Y-86,21022 in shake flasks

Composition of seed medium I

| | |
|---|---|
| Glucose | 15.0 g |
| Soyabean meal | 15.0 g |
| Corn steep liquor | 5.0 g |
| CaCO$_3$ | 2.0 g |
| Demineralized water | 1000 ml |
| pH | 7.0 |

The above seed medium was distributed in 80 ml amounts in 500 ml Erlenmeyer flasks and autoclaved for 20 minutes, The flasks were cooled to room temperature and each flask was then inoculated with a loopful of the above mentioned well grown culture of Example 2 and shaken on a rotary shaker for 72 hours at 240 rpm at 29° C. (±1° C.) to give seed culture.

Composition of the production medium

| | |
|---|---|
| Glycerol | 15.0 g |
| Soyabean meal | 10.0 g |
| CaCO$_3$ | 1.0 g |
| NaCl | 5.0 g |
| CoCl$_2$ | 0.001 g |
| Demineralized water | 1000 ml |
| pH | 7.0 |

The production medium was distributed in 60 ml amounts in 500 ml Erlenmeyer flasks and autoclaved at 121° C. for 20 minutes. The flasks were cooled and then inoculated with the above mentioned seed culture (1% v/v). The fermentation was carried out on a rotary shaker at 240 rpm and at a temperature of 29° C. (±1° C.) for 68 hours.

The production of the antibiotic was determined by HPLC and by testing the bioactivity against *S. aureus* 3066 using the well diffusion method in a known manner. After harvesting, the culture broth was centrifuged and Balhimycin isolated from the culture filtrate and purified as described in Example 4.

EXAMPLE 4

Cultivation of the culture No. Y-86,21022 in fermenters

Preparation of seed culture in shake flasks

The seed medium of Example 3 was distributed in 160 ml amounts in 1 L Erlenmeyer flasks and autoclaved for 20 minutes. The seed culture was grown in these flasks as described in Example 3.

Large Scale Fermentation

| | |
|---|---|
| Glycerol | 15.0 g |
| Soyabean meal | 10.0 g |
| CaCO$_3$ | 1.0 g |
| NaCl | 5.0 g |
| Demineralized water | 1000 ml |
| pH | 6.8 |

100 liters of the production medium in 150 liter Marubishi fermenter along with 30 ml of Desmophen as antifoam was sterilized in situ for 24 minutes at 121° C. cooled to 29°±1° C. and seeded with 3 liters of the seed culture mentioned above.

The fermentation was run with the following parameters:

| | |
|---|---|
| Temperature | 29° C. (±.5° C.) |
| Agitation | 110–120 rpm |
| Aeration | 80–100 epm |
| Harvest time | 69–72 hrs |

The production of the antibiotic was monitored by the bioactivity against *S. aureus* 3066. When fermentation was discontinued, the pH of the culture broth was 6.0–7.0. The culture broth was centrifuged after harvesting and the antibiotic Balhimycin was isolated and purified from the culture filtrate as described below.

Isolation and purification of Balhimycin

Approximately 100 L of the harvested broth, as obtained in Example 4, was separated from the mycelium by centrifugation. The resulting broth filtrate (80 L, pH 6.5) was passed through a column of 5 L of 1 Diaion HP-20, in water. The column was washed with 40 L of demineralized water after which the washings were colourless. The column was then washed with 8 L of 1M aqueous NaCl followed by 10 L of demineralized water. This process was repeated once. The column was then washed with 9 L of 30% MeOH in water and finally eluted with 51 L of 75% MeOH in water collected in fractions of 1 L size. The presence of Balhimycin in these eluates was monitored by its activity against *Staphylococcus aureus* 3066 which is a methicillin resistant organism. The combined active eluates were concentrated under vacuo at 40°–45° C. to approximately 1 L which was then lyophilized to give 38 g of crude Balhimycin as a powder.

The above mentioned crude material was then subjected in three batches of 10 g each to medium pressure liquid chromatography (MPLC) on RP-18 packed in a 6.5×55 cm glass column having a bed volume of 1.2 L. The column was eluted with 2 L of water containing 0.1% trifluoroacetic acid (TFA), followed by elution with 5% acetonitrile (4 L), 7.5% acetonitrile (9 L) and 10% acetonitrile (24.5 L) in water containing 0.1% TFA. Balhimycin eluted out in 10% acetonitrile eluates which were collected in fractions of 500 ml and monitored by in vitro antibiotic activity. The combined active eluates were concentrated under high vacuum at 40° C. and then lyophilized to give 2.1 g of Balhimycin as a pale yellow powder. Three such processes gave a total of 6.3 g of semi-pure Balhimycin from the 30 g of the crude material.

The 6.3 g of semi-pure Balhimycin thus obtained was finally purified by subjecting in three batches of 2.1 g each to MPLC on RP-18 in a 6.0×45 mm glass column with a bed volume of 500 mL. The column was washed with 1 L of water containing 0.1% TFA followed by 2 L and 1.5 L of 5% and 7.5% acetonitrile respectively in water containing 0.1% TFA. Balhimycin eluted out in 10% acetonitrile in water containing 0.1% TFA, the fractions of 250 ml each were monitored both by a UV detector working at 220 nm and by in-vitro antibiotic assay. A total of 8 L of active eluates were concentrated under high vacuum at 40° C. followed by lyophilization to give 600 mg of Balhimycin as a trifluoroacetate salt in the form of white powder. From the 6.3 g of semi-pure Balhimycin, 1.8 g of pure Balhimycin was procured.

Biological properties of Balhimycin

The antibacterial activity of Balhimycin as MIC values required to inhibit the growth of various bacteria are shown in Table II.

TABLE II

Minimum inhibitory concentrations (MIC) of Balhimycin trifluoroacetate

| Test Organism | MIC (mcg/ml) |
|---|---|
| *S. aureus* 209 P | 0.39 |
| *S. aureus* (MethR) | 0.39 |
| *S. aureus* 3066 (MethR) | 0.78 |
| *S. aureus* E 690 (MethR) | 0.39 |
| *Streptococcus faecalis* ATCC 29212 | 1.56 |
| *S. faec.* D 21777 | 0.78 |
| *S. faec.* D Endococcen | 0.78 |
| *S. faecium* D-59 | 1.56 |
| *S. faecium* D-65 | 0.78 |
| *Staph. epidermidis* 178 | 1.56 |
| *S. epi.* 825 | 3.12 |
| *S. epi.* 823 (Teicoplanin$^R$) | 12.5 |
| *Staph. haemolyticus* 712 | 1.56 |
| *S. haemo.* 809 (Teicoplanin$^R$) | 6.25 |
| *E. coli* 9632 | >100 |
| *P. vulaaris* | >100 |
| *Ps. aeruaingu* | >100 |

We claim:

1. A process for the preparation of Balhimycin

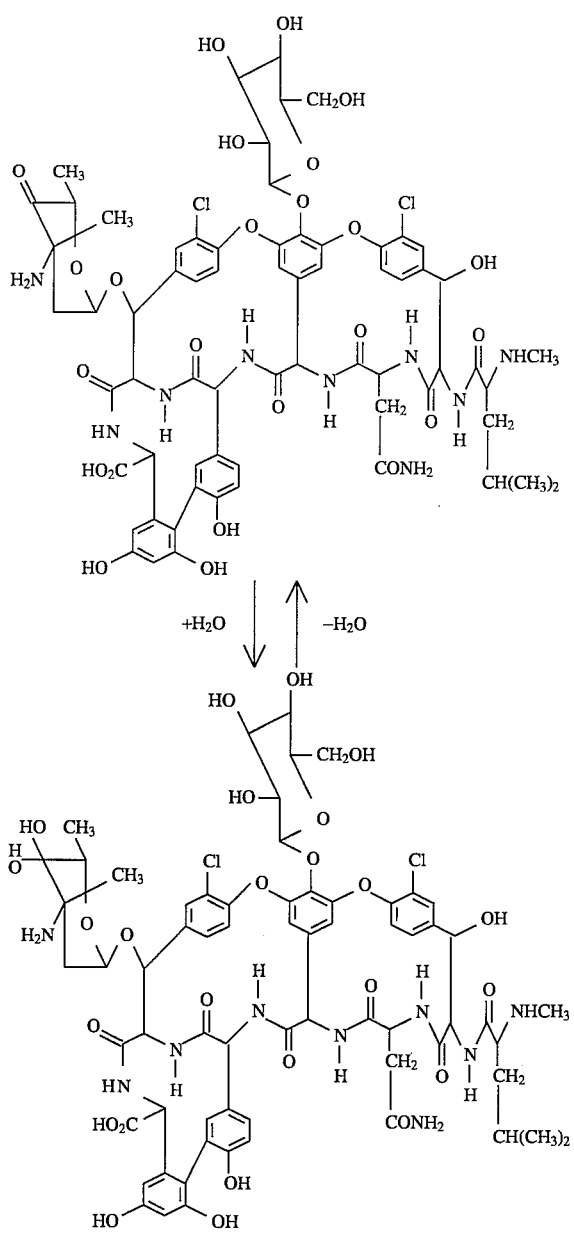

which comprises fermentation of Actinomycete species Y-86,21022 (DSM 5908), and the mutants thereof, cultivated under aerobic conditions in a nutrient medium containing sources of carbon and of nitrogen, inorganic nutrient salts and trace elements, and isolation and purification of the compound from the culture broth.

2. The process as claimed in claim 1, wherein the cultivation is carried out at temperatures between about 28° and 32° C. and at a pH between about 6 and 8.

3. The process as claimed in claim 1, wherein the cultivation is carried out at 29° C. (±1° C.) and a pH about 7.0.

4. The process as claimed in claim 1, wherein the fermentation is carried out for 68 to 72 hours.

5. The process as claimed in claim 1, wherein the fermentation is carried out at submerged fermentation.

6. The process of claim 1 wherein said carbon source is selected from the group consisting of starch, glucose, sucrose, dextrin, fructose, molasses, glycerol, lactose or galactose.

7. The process of claim 6 wherein said carbon source is glycerol.

8. The process of claim 1 wherein said nitrogen source is soyabean meal, peanut meal, yeast extract, beef extract, peptone, malt extract, corn steep liquor, gelatin or casamino acids.

9. The process of claim 8 wherein said nitrogen source is soyabean meal.

10. Isolated Actinomycete species Y-86,21022 (DSM 5908).

* * * * *

UNITED STATES PATENT AND TRADEMARK OFFICE
CERTIFICATE OF CORRECTION

PATENT NO. : 5,571,701
DATED : November 05, 1996
INVENTOR(S) : Suresh R. NADKARNI et al.

It is certified that error appears in the above-indentified patent and that said Letters Patent is hereby corrected as shown below:

Title page, Item [75], Inventors, line 4, delete "L.B.S. Mang".

Signed and Sealed this

Thirtieth Day of September, 1997

Attest:

BRUCE LEHMAN

*Attesting Officer*    *Commissioner of Patents and Trademarks*